（12) United States Patent
Cheng et al.

(10) Patent No.: US 10,716,758 B2
(45) Date of Patent: Jul. 21, 2020

(54) LIPOSOMAL STATIN FORMULATION

(71) Applicants: Southwest Research Institute, San Antonio, TX (US); Northwestern University, Evanston, IL (US)

(72) Inventors: XingGou Cheng, San Antonio, TX (US); Thomas A. Mustoe, Evanston, IL (US); Robert D. Galiano, Glenview, IL (US); Seok Jong Hong, Northbrook, IL (US); Ping Xie, Chicago, IL (US); Shengxian Jia, Wilmette, IL (US)

(73) Assignees: SOUTHWEST RESEARCH INSTITUTE, San Antonio, TX (US); NORTHWESTER UNIVERSITY, Evanston, IL (US)

( * ) Notice: Subject to any disclaimer, the term of this patent is extended or adjusted under 35 U.S.C. 154(b) by 0 days.

(21) Appl. No.: 15/949,000

(22) Filed: Apr. 9, 2018

(65) Prior Publication Data
US 2019/0307693 A1    Oct. 10, 2019

(51) Int. Cl.
| A61K 9/127 | (2006.01) |
| A61K 47/26 | (2006.01) |
| A61K 31/366 | (2006.01) |
| A61K 9/00 | (2006.01) |

(52) U.S. Cl.
CPC .......... *A61K 9/1278* (2013.01); *A61K 9/0014* (2013.01); *A61K 31/366* (2013.01); *A61K 47/26* (2013.01)

(58) Field of Classification Search
CPC ...... A61K 9/127; A61K 9/0014; A61K 31/22; A61K 31/366
See application file for complete search history.

(56) References Cited

U.S. PATENT DOCUMENTS

| 2004/0014782 A1* | 1/2004 | Krause | A61K 31/16 514/313 |
| 2006/0110441 A1* | 5/2006 | Wong | A61K 9/127 424/450 |
| 2008/0026049 A1* | 1/2008 | Wasan | A61K 9/1271 424/450 |
| 2009/0092663 A1* | 4/2009 | Ponzoni | A61K 9/127 424/450 |
| 2009/0136563 A1* | 5/2009 | Kogure | A61K 9/127 424/450 |
| 2010/0143453 A1* | 6/2010 | Schiffelers | A61K 9/1271 424/450 |
| 2010/0247447 A1* | 9/2010 | Boch | A61K 9/1075 424/9.61 |
| 2011/0105996 A1 | 5/2011 | Mustoe et al. | |
| 2011/0117187 A1* | 5/2011 | Stock | A61K 31/198 424/450 |
| 2012/0189678 A1* | 7/2012 | Li | A61K 9/1271 424/401 |
| 2017/0119732 A1 | 5/2017 | Mustoe et al. | |

OTHER PUBLICATIONS

Tuerdi N., et al in Nanomedicine Nanotechnology, Biology and Medicine, vol. 12, pp. 1899-1907, 2016.*
Porfire A., et al in Saudi Pharmaceutical Journal, vol. 25, # 7, Nov. 2017, pp. 981-992.*
Pick, U., Archives of Biochemistry and Biophysics, vol. 212, # 1, pp. 186-194, 1981.*
Afergan, E., et al: "Liposomal Simvastatin Attenuates Neointimal Hyperplasia in Rats"; The AAPS Journal, vol. 12, No. 2, Jun. 2010, pp. 181-187.
AFIRM (Armed Forces Institute of Regenerative Medicine); Annual Report 2014 (130 pgs).
Alupei, M.C., et al; "Liposomal Simvastatin Inhibits Tumor Growth via Targeting Tumor-associated Macrophages-mediated Oxidative Stress". Cancer Letters 356 (2015), pp. 946-952.
Campos-Martorell, M,, et al: "Charge Effect of a Liposomal Delivery System Encapsulating Simvastatin to Treat Experimental Ischemic Stroke in Rats"; International Journal of Nanomedicine, Dove press. 2016;11 pp. 3035-3048.
Clementino, A., et al. "The Nasal Delivery of Nanoencapsulated Statins—an Approach for Brain Delivery"; International Journal of Nanomedicine. Dovepress 2016;11 pp. 6575-6590.
Csempesz, F., et al, "Induced Surface Activity of Supramolecular Cyclodextrin—Statin Complexes: Relevance in Drug Delivery". Colloids and Surfaces A: Physicochemical and Engineering Aspects. 2010; 354 pp. 308-313.
Jia, S., et al; DoD-funded project within Armed Force Institute of Regenerative Medicine (AFIRM) entitled "Local Application of Statins Significantly Reduced Hypertrophic Scarring in a Rabbit Ear Model"; PRS (Plastic and Reconstructive Surgery) Global Open Experimental 2017 (9 pgs).
Ko, J.H., et al "HMG-CoA Reductase Inhibitors (Statins) Reduce Hypertrophic Scar Formation in a Rabbit Ear Wounding Model"; Plastic and Reconstructive Surgery vol. 129, No. 2 Statins Reduce Hypertrophic Scar in Vlvo; Feb. 2012; pp. 252e-261e.
Suresh, G., et al; "Preparation, Characterization, and In Vitro and In Vivo Evaluation of Lovastatin Solid Lipid Nanoparticles". AAPS PharmSciTech. 2007;8(1): Article 24 pp. E1-E9.
Ungaro, F., et al; "Use of Cyclodextrins as Solubilizing Agents for Simvastatin: Effect of Hydroxypropyl-Beta-Cyclodextrin on Lactone/Hydroxyacid Aqueous Equilibrium". International Journal of Pharmaceutics, 2011;404; pp. 49-56.

(Continued)

*Primary Examiner* — Kortney L. Klinkel
(74) *Attorney, Agent, or Firm* — Grossman, Tucker, Perreault & Pfleger, PLLC

(57) ABSTRACT

A method of preparing liposomal statins includes preparing a lipid solution including phosphatidylcholine, cholesterol, vitamin-E and an organic solvent and removing the solvent, forming a lipid cake. The lipid cake may then be hydrated with a first aqueous media. The hydrated cake may be mixed in a mixer and subjected to one or more freeze/thaw cycles and then extruded to form liposomes. A cryo-protective agent may be added to the liposomes and the liposomes may be lyophilized to provide a powder. A statin is added to the organic lipid solution or to the first aqueous media used for hydrating the lipid cake.

18 Claims, 21 Drawing Sheets

(56) References Cited

OTHER PUBLICATIONS

Zhang, Z., et al; "The Characteristics and Mechanism of Simvastatin Loaded Lipid Nanoparticles to Increase Oral Bioavailability in Rats". International Journal of Pharmaceutics, Pharmaceutical Nanotechnology 2010;394 pp. 147-153.
Zhou, J, & Zhou, D.' "Improvement of Oral Bioavailability of Lovastatin by Using Nanostructured Lipid Carriers"; Drug Design, Development and Therapy. 2015;9: pp. 5269-5275.
Zidan, A.S,, et al; "Assessment of Simvastatin Niosomes for Pediatric Transdermal Drug Delivery". InformaHealthCare, Drug delivery. 2016;23(5): pp. 1536-1549.

\* cited by examiner

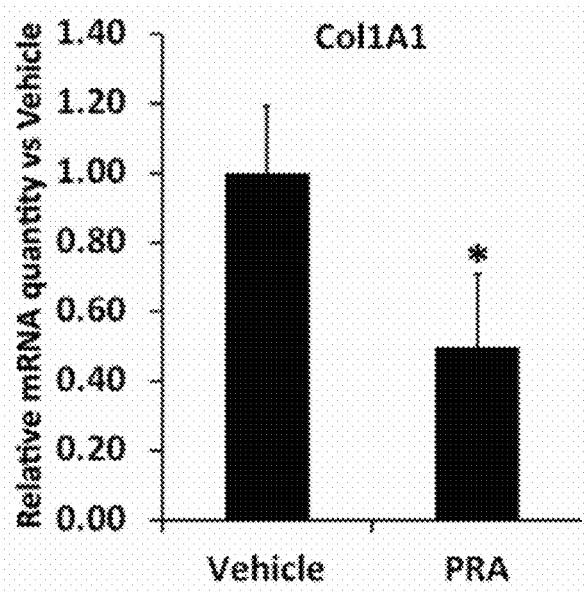
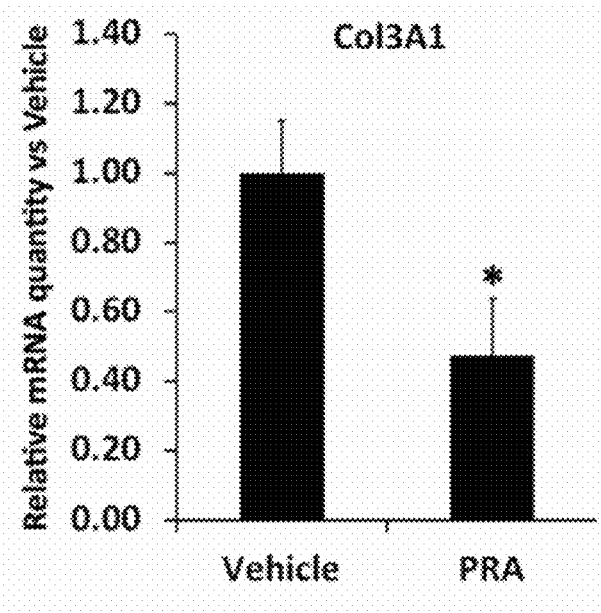
*FIG. 10b*          *FIG. 10c*

LIPOSOMAL STATIN FORMULATION

GOVERNMENT SUPPORT CLAUSE

This invention was made with United States Government support under Contract No. W81XWH-13-2-0052 awarded by the U.S. Army Medical Research Acquisition Activity. The Government has certain rights in this invention.

FIELD

The present disclosure is directed to liposomal statin formulation and, particularly, a method of producing a liposomal statin formulation.

BACKGROUND

Statins, 3-Hydroxy-3-methylglutaryl-coenzyme A reductase inhibitors, are often used to lower LDL cholesterol in patients and for protection from atherosclerotic cardiovascular disease, reducing plaque formation in blood vessels and resultant coronary morbidity and mortality in relatively high risk adults. Statins may also be used for pediatric populations with dyslipidemia, the elevation of plasma cholesterol, triglycerides, or both.

It has been found that relatively low doses (40 µM) of simvastatin, lovastatin, and pravastatin each demonstrated reduction in the scar elevation index when compare with a control in a rabbit ear model, which has been described in U.S. patent application Ser. No. 15/407,747, filed Jan. 17, 2017 and now published as US Patent Application Publication Number 2017/0119732. It is desirable to develop compositions that may be applied to and can penetrate the skin and scar tissue. However, the statins exhibit various levels of solubility in water and the previous study reports the use of solvents such as dimethyl sulfoxide (DMSO) or surfactants, which may be relatively toxic and could potentially hinder FDA approval.

Various efforts have been made to improve solubility of the statins. One method involves the complexation of cyclodextrin (CD) with simvastatin or lovastatin. Another method includes the formation of solid lipid nanoparticles of statin. A further method includes a transdermal niosomes formulation, which contains skin penetrating enhancing surfactants (e.g., Span 20 or Span 60), surface charge imparting agents (e.g., stearylamine or dicetyl phosphate), cholesterol and simvastatin.

Additional liposomal statin formulations have been reported. For example, a liposome simvastatin formulation mainly composed of distearoylphosphatidylcholine (DSPC), distearoyl phosphatidyl glycerol (DSPC, DSPG, Cholesterol:simvastatin at 7:3:1:1 molar ratio) has been reported. Alupei MC formulated liposomal simvastatin and found that it can reduce tumor growth via targeting tumor-associated macrophages-mediated oxidative stress. This liposome statin formulation involves a lipid composition of 1,2-dipalmitoyl-sn-glycero-3-phosphocholine (DPPC) (Lipoid GmbH, Ludwigshafen, Germany), polyethylene glycol 2000-distearoylphosphatidylethanolamine (PEG-2000-DSPE), (Lipoid GmbH, Ludwigshafen, Germany), cholesterol (Sigma, St. Louis, USA) and simvastatin (Sigma, St. Louis, USA) in a molar ratio of 17:1.011:1:1.209. This liposomal simvastatin was administrated intravenously (i.v.). Another liposome simvastatin formulation is composed of 1,2-Didodecanoyl-sn-glycero-3-phosphocholine (DLPC) Cholesterol, cholesteryl-polyethylene glycol 600 sebacate (CHOL-PEG), and 1,2-dioleoyl-sn-glycero-3-phosphoric acid monosodium salt (DOPA). Cholesteryl 3β-N-(dimethylaminoethyl) carbamate hydrochloride (CHOL+) and 1,2-dioleoyl-sn-glycero-3-phosphoethanolamine (DOPE). However, liposome formulations for both relatively soluble and insoluble formations are desired, wherein the formulations provide an increase in solubility of the statins.

SUMMARY

An aspect of the present disclosure relates to a method of preparing liposomal statins. The method includes preparing a lipid solution including phosphatidylcholine, cholesterol, vitamin-E and an organic solvent and removing the solvent and forming a lipid cake. The lipid cake may then be hydrated with a first aqueous media. The hydrated cake may be mixed in a mixer, subjected to one or more freeze/thaw cycles and then extruded to form liposomes. A cryo-protective agent may be added to the liposomes and the liposomes may be lyophilized to provide a powder. A statin is added to the organic solvent lipid solution or to the first aqueous media used for hydrating the lipid cake.

Another aspect of the present disclosure relates to a method of applying a liposomal statin formulation. The method includes providing a topical formulation of liposomal statins comprising phosphatidylcholine present in the range of 15 to 40 wt %, cholesterol present in the range of 1 to 5 wt %, vitamin-E present in the range of 0 to 5 wt %, a skin penetrator present in the range of 2 to 15 wt %. The liposome formulation may also include a cryoprotector present in the range of 0 to 15 wt % in the reconstituted liquid form, and load one or more statins present in the range of 0.1 wt % to 10 wt %, and the balance aqueous media, wherein the formulation is selected to equal 100 wt %, and applying the formulation onto a subject.

A further aspect of the present disclosure relates to a formulation of liposomal statins. The formulation includes phosphatidylcholine present in the range of 15 to 40 wt %, cholesterol present in the range of 1 to 5 wt %, vitamin-E present in the range of 0 to 5 wt %, a skin penetrator present in the range of 2 to 15 wt %, a cryoprotector present in the range of 0 to 15 wt %, and a statin present in the range of 0.1 wt % to 10 wt % and the balance aqueous media.

BRIEF DESCRIPTION OF DRAWINGS

The above-mentioned and other features of this disclosure and the manner of attaining them will become more apparent with reference to the following description of embodiments herein taking in conjunction with the accompanying drawings, wherein:

FIG. 10b is a graph of the relative mRNA quantity of Col 1A1;

FIG. 10c is a graph of the relative mRNA quantity of Col 3A1;

DETAILED DESCRIPTION

Figure 1:
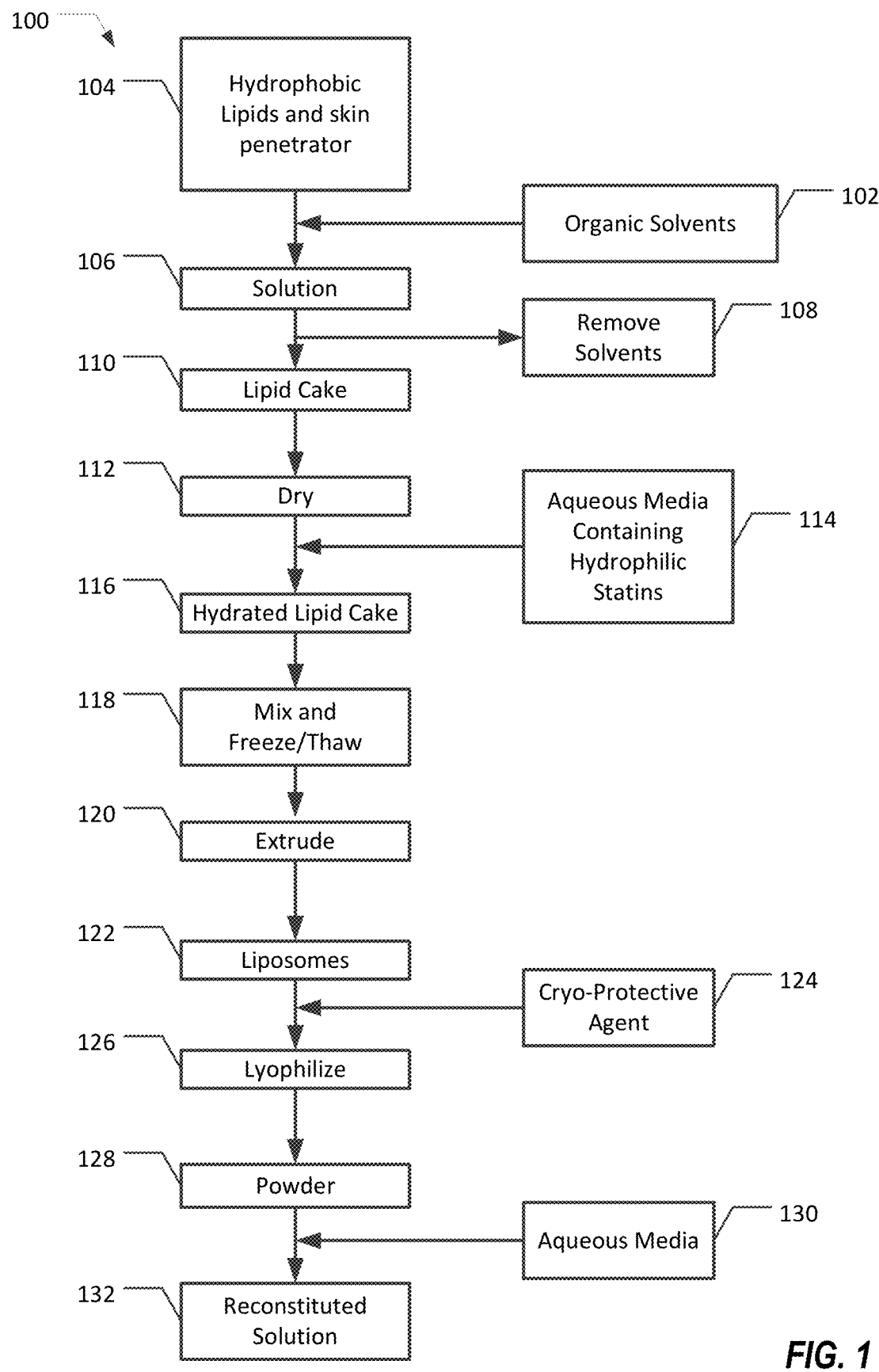
FIG. 1 illustrates a flow chart of an embodiment of providing the liposomal statins.

The present disclosure is directed to liposomal statin formulations preferably including one or more of simvastatin, lovastatin and pravastatin that may be utilized for the reduction of scar tissue as well as for the treatment of other conditions, including, but not limited to, burn skin wound healing, dyslipidemia, skin cancer, Ischemic stroke, and cardiovascular protection. The formulations may particularly include topical formulations or lyophilized powder that may be reconstituted.

Various statins may be employed for use herein, both hydrophobic and hydrophilic, and particularly, simvastatin, lovastatin and pravastatin. Hydrophobic statins may be understood as statins that are insoluble in water. Hydrophilic statins are understood herein as statins that are soluble in water in an amount of 30 mg/ml or higher. Solubility of less than 30 mg/ml may be considered as having relatively low solubility and hydrophobic. Solubility herein is that solubility determined at a temperature in the range of 20° C. to 25° C. Simvastatin is available as a crystalline powder with a melting point of 135 to 138° C. and is reportedly insoluble in water and is considered herein as a hydrophobic statin. Lovastatin is understood to exhibit relatively low solubility in water, reportedly 0.0004 mg/mL and is also considered herein as a hydrophobic statin. Pravastatin is reported as being soluble in water and is considered herein as a hydrophilic statin.

The statins are incorporated into a liposomal statin formulation. The liposomal statin formulation preferably includes phosphatidylcholine, cholesterol, and vitamin-E (e.g., α form) as lipids. The phosphatidylcholine is preferably sourced form soybeans or egg yolk, or preferably other sources. The liposomal statin formulation may also include a skin penetrating enhancer, which may be understood as molecules that enhance the penetration of liposome across skin barrier (e.g., stratum corneum). In embodiments, the liposomal statin formulation may be available as a powder.

The powder may be reconstituted to provide the liposomal statin formulation in aqueous media, which may be used as a topical formulation. The phosphatidylcholine may be present in the range of 15 wt. % to 40 wt. % of the total solution, including all values and ranges therein. The cholesterol may be present from 1 wt. % to 5 wt. % of the total solution, including all values and ranges therein and preferably in the range of 2 wt. % to 4 wt. %. Vitamin-E, preferably in a form, is optionally present from 1 wt. % to 5 wt. % of the total solution, including all values and ranges therein, and, thus, may at times may be excluded. The skin penetrator may include Span 20, Span 60 or, preferably, sodium cholate, which may be present in the range of 2 wt. % to 15 wt. % of the total solution, including all values and ranges therein. The statins may be present in the range of 0.1 wt. % to 10 wt. % of the total weight of the solution, including all values and ranges therein. Further, the solution may include optionally cryo-protective agent, such as sucrose or trehalose, present in the range of 0 wt. % to 15 wt. % of the total weight of the solution, including all values and ranges therein and preferably in the range of 5 wt % to 15 wt %. The remainder of the solution includes aqueous media.

Optionally, one may consider the incorporation of other hydrophilic or hydrophobic drugs or compositions into the lipid bi-layer of the formulation. For example, one may incorporate linoleic acid or fatty acids such as Omega-3 or Omega-6. Hydrophilic drugs or compositions may include Vitamin C, proteasome inhibitor such as MG-132 or water soluble polypeptides.

The method of formulating the liposomal statin formulation 100, as illustrated in flow chart FIG. 1, generally includes adding a solvent 102 containing a hydrophobic statin to the lipids (i.e., the phosphatidylcholine, cholesterol, and vitamin-E) and a skin penetrator 104 to prepare a solution 106. The solvents preferably include chloroform, methanol, or a combination thereof at a 1:1 ratio. In addition, if the statins are hydrophobic the statins are preferably provided with the lipids at this stage 104. Accordingly, in the broad context of the present invention, the solvent used to introduce the hydrophobic statins are organic (carbon-based) based solvents.

The solvent is preferably removed 108 to form a lipid cake 110. The solvents may be removed using an evaporation system such as a nitrogen blow down dry evaporator or a rotary evaporator. The lipid cake may then be further dried 112 by, e.g., vacuum drying. Aqueous media 114, such as water, or a phosphate buffered solution or aqueous saline solution, is then added to the cake to hydrate the cake 116. If the statins are hydrophilic, they may be added with the aqueous media 114 at this stage. It may be appreciated that more than one statin may be incorporated into the liposomes, including hydrophobic and hydrophilic statins.

The hydrated cake may be mixed in a vortex mixer and exposed to one or more freeze/thaw cycles (such as in the range of 3 to 10 cycles) 118. Freezing may be facilitated by, e.g., liquid $N_2$ and thawing may be facilitated by, e.g., a 40° C. sonicator bath. The thawed solution is preferably then extruded one or more times (such as in the range of 1 to 20) 120 through one or more membranes to form liposomes 122. The extruder used may be, e.g., a LIPEX extruder, available from Transferra. In preferred embodiments, two membranes are used, a 0.2 μm (e.g., WHATMAN® polycarbonate track-etch) membrane and a 0.1 μm membrane. A cryoprotecting agent, such as sucrose 124 is then preferably added to the liposomes and the liposomes may be flash frozen using liquid nitrogen and is then lyophilized 126 into a liposomal statin powder 128. The liposomal statin may exhibit powder may exhibit a particle size in the range of 1 to 200 nm, including all values and ranges therein, and particularly 30 to 60 nm or 130 nm to 200 nm. The liposomal statin powder may then be rehydrated with an aqueous media 130 to form a reconstituted solution 132 of the liposomal statin(s).

In embodiments, the liposomal statin(s) may be shipped either as powder, as a reconstituted solution, or combined with secondary topical treatments such as silicone gel (e.g., KELO-COTE available from Senvie Skin Care), 2-(2-ethoxyethoxy)ethanol (e.g. TRANSCUTOL available from Gattefossé) or glyceryl caprylate/caprate (e.g., CAPMUL MCM EP available from ABITEC corporation). The liposomal statin(s) may be applied topically onto a subject, and preferably onto a wound. Topical application of the formulation may be understood as the application of the liposomes (powdered, reconstituted or incorporated into a secondary topical treatment) onto the skin or mucosal membranes of the subject. Wounds may be understood as an injury to tissue, including but not limited to the skin or mucosal membranes, wherein the injury may include the damage or breach of the tissue. A subject may be understood as a human or other mammal, such as rabbits, mice, dogs, etc.

The liposomal statins were found to reduce scarring, including the color/shade of the scar, as determined by the scare elevation index. Further, the liposomes were found to provide collagen I to collagen III ratios that were closer to that of non-wounded skin and reduced mRNA levels of Col1A1, Col3A1, MMP9, TIMP1, TGFbeta, and connective tissue growth factor (CTFG), which contribute to scare formation. In addition, the liposomal statin increased the MMP1 (collagenase). In addition to applications for scar reduction, the liposomal statins may be also used for treatment of other diseases including, but not limited to, burn skin wound healing, dyslipidemia, skin cancer, Ischemic stroke, and cardiovascular protection.

EXAMPLES

Example 1: Liposome Statin Formulation with 2% Cholesterol and 6.5% Pravastatin

Phosphatidylcholine (Lipoid S-100) (588 mg), cholesterol (40 mg), Vitamin-E (54 mg) and sodium cholate (150 mg) were dissolved in $CHCl_3$:MeOH (1:1) to form a transparent solution in a round flask or 50 mL large vial. The solvent was removed by a rotary evaporator or a nitrogen blow down dry evaporator to form a lipid cake. The cake was further vacuum dried overnight to remove residual solvent. This cake was hydrated with pravastatin solution (e.g., 130 mg pravastatin in 12 mL endotoxin-free water). The solution was vortexed and subjected to repeated freeze (liquid $N_2$) and thaw (using 40° C. sonicator bath) five times. The final thawed solution was then extruded using Lipex extruder 10 times through the 0.2 μm membrane and 0.1 μm membrane, respectively. 12 mL of liposomes was added 0.2 g of sucrose, flash frozen using liquid $N_2$, and lyophilized into powder. The powder was reconstituted with 2 mL aqueous media (e.g., $H_2O$). The liposome solution containing 6.5 wt. % pravastatin and 2 wt. % cholesterol was obtained. This formulation was tested in rabbit ear model and shown to reduce hypertrophic scar in a rabbit ear model, discussed further below.

Example 2: Liposome Statin Formulation with 3.75% Cholesterol and 6.5% Simvastatin Phosphatidylcholine (Lipoid S-100) (588 mg), cholesterol (75 mg), Vitamin-E (54 mg) and sodium cholate (150 mg), and 130 mg of simvastatin were dissolved in $CHCl_3$:MeOH (1:1) to form a transparent solution in a round flask or 50 mL large vial. The solvent was removed by rotary evaporator or a nitrogen blow down dry evaporator to form a lipid cake. The cake was further vacuum dried overnight to remove residual solvent. The cake was hydrated with up to 12 mL endotoxin-free water. The solution was vortexed and exposed to repeated freeze (liquid $N_2$) and thaw (using 40° C. sonicator bath) five times. The final thawed solution was then extruded using a Lipex extruder 10 times through the 0.2 μm membrane and 0.1 μm membrane, respectively. 12 mL of liposomes was added 0.2 g of sucrose, flash froze using liquid $N_2$, and lyophilized into powder. The powder was reconstituted with 2 mL aqueous media (e.g., $H_2O$). The resulting liposome statin solution contained 6.5 wt. % simvastatin and 3.75 wt. % cholesterol. This formulation was tested in rabbit ear model and shown to reduce hypertrophic scar in a rabbit ear model, discussed further below. The loading efficiency of simvastatin in liposome is nearly 100% as simvastatin is practically insoluble in water and we did not observe any white precipitate on the membrane, suggesting all simvastatin was loaded into the hydrophobic lipid bi-layer.

Example 3: Liposome Statin Formulation with 3.75% Cholesterol, 6.5% Simvastatin, and 6.5 Pravastatin Phosphatidylcholine (Lipoid S-100) (588 mg), cholesterol (75 mg), Vitamin-E (54 mg) and sodium cholate (150 mg), and 130 mg of simvastatin were dissolved in about 5 mL of $CHCl_3$:MeOH (1:1) to form a transparent solution in a round flask or 50 mL large vial. The solvent was removed by a rotary evaporator or a nitrogen gas blow to form a lipid cake. The cake was further vacuum dried overnight to remove residual solvent. This cake was hydrated with hydrated with pravastatin solution (e.g., 130 mg pravastatin in 12 mL endotoxin-free water). The solution was vortexed and exposed to repeated freeze (liquid $N_2$) and thaw (using 40° C. sonicator bath) five times. The final thawed solution was then extruded using a Lipex extruder 10 times through the 0.2 μm membrane and 0.1 μm membrane, respectively. 12 mL liposomes was added 0.2 g of sucrose, flash freeze using liquid N$_2$ and lyophilized into powder. The powder was reconstituted with 2 mL aqueous media (e.g., H$_2$O). The liposome solution contained 6.5 wt. % simvastatin, 6.5 wt. % pravastatin, and 3.75 wt. % cholesterol. While this formulation was not tested, it showed that both hydrophobic statin and hydrophilic stain can be loaded into liposomes together using one formulation.

Example 4: Liposome Statin Formulation with 3.75% Cholesterol and 2.1% Lovastatin Phosphatidylcholine (Lipoid S-100) (705 mg), cholesterol (48 mg), Vitamin-E (65 mg) and sodium cholate (180 mg), and 42 mg of lovastatin were dissolved in about 5 mL of CHCl$_3$:MeOH (1:1) to form a transparent solution in a round flask or 50 mL large vial. The solvent was removed by a rotary evaporator at 40° C. or a nitrogen gas blow at room temperature to form a lipid cake. The cake was further vacuum dried overnight to remove residual solvent. This cake was hydrated with up to 14.4 mL endotoxin-free water. The solution was vortexed and exposed to repeated freeze (liquid N$_2$) and thaw (using 40° C. sonicator bath) five times. The final thawed solution was then extruded using a Lipex extruder 10 times through the 0.2 μm membrane and 0.1 μm membrane, respectively. 14 mL of liposomes was added 0.2 g of sucrose, flash freeze using liquid N$_2$ and lyophilized into powder. The powder was reconstituted with 2 mL aqueous media (e.g., H$_2$O). The liposome solution contained 2.1 wt. % lovastatin and 2.4 wt. % cholesterol.

Example 5: Particle Size Analysis of Liposome Statin Formulation of Example 1

Figure 2:
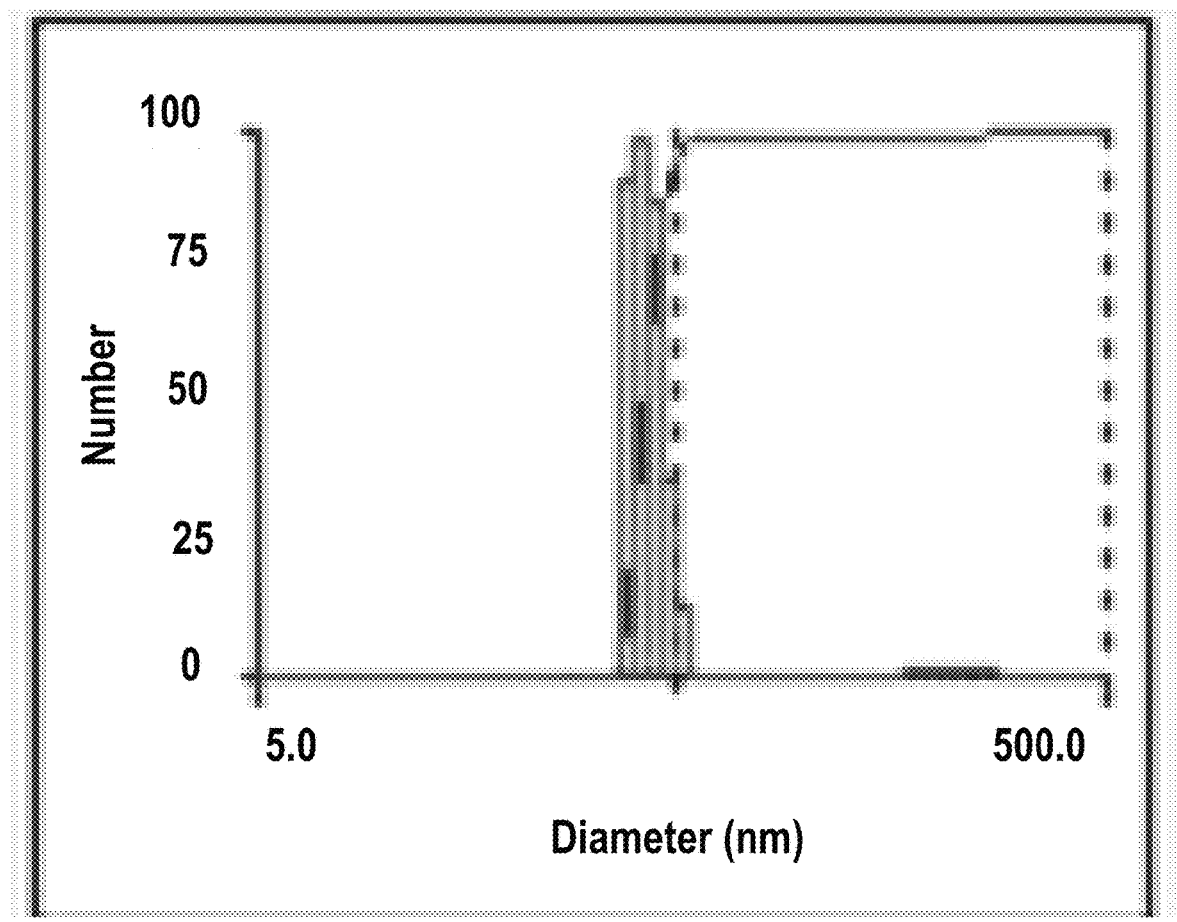
FIG. 2 illustrates a graph quantifying the mean diameter of the particles formulated with Example 1.
Figure 3:
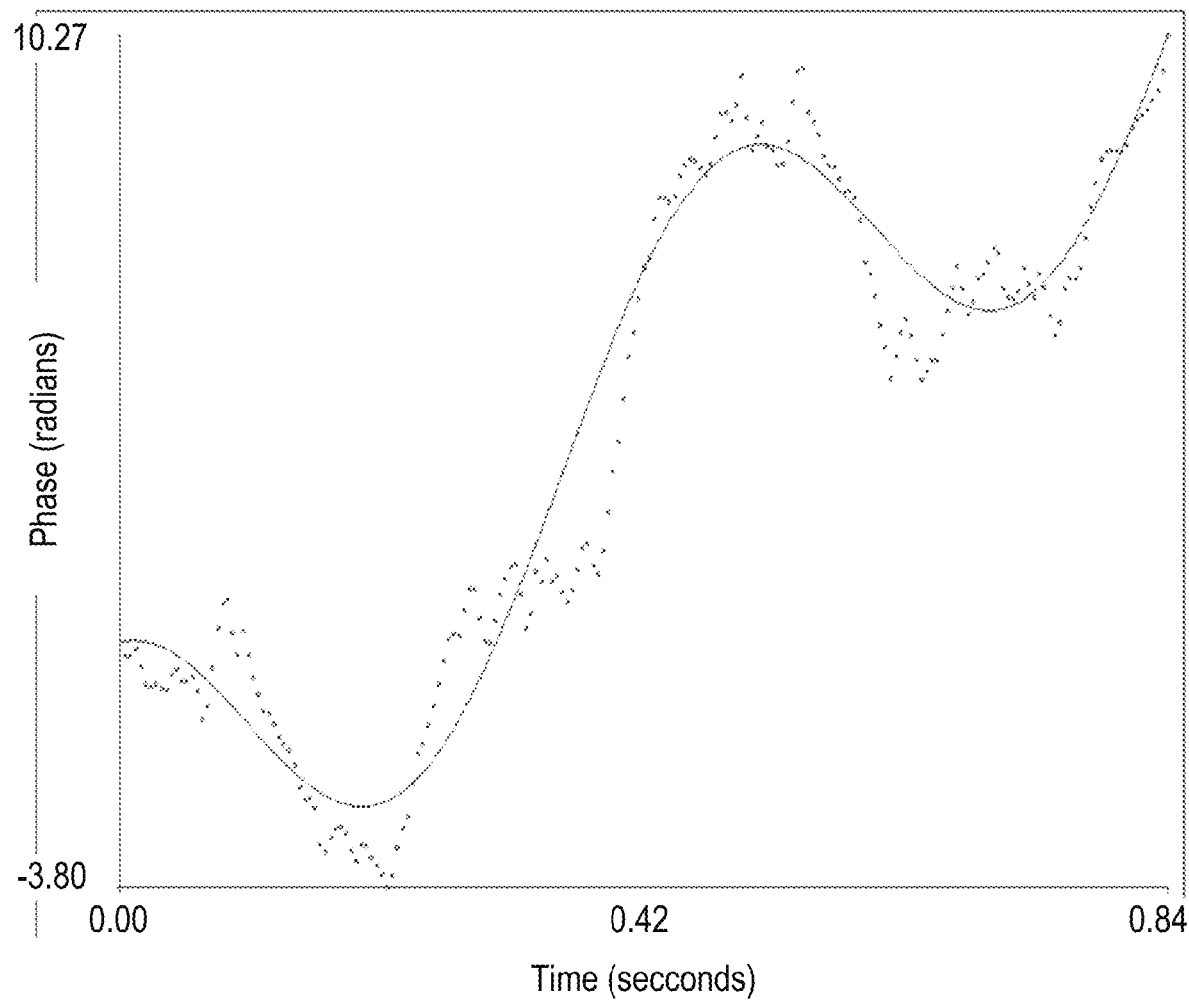
FIG. 3 illustrates a graph quantifying the zeta potential of the particles formulated with Example 1.

The liposome statin particles of example 1 were found to exhibit a mean diameter (largest linear dimension) of around 41.2 nm with a relative variation of 0.036 measured using a Brookhaven particle sizer. Data from the testing is provided in Table 1, below, and illustrated in FIG. 2. The zeta-potential was determined to be around −26 mV and is graphed in FIG. 3.

TABLE 1

| Particle size measurements | | |
|---|---|---|
| d (nm) | G (d) | C (d) |
| 26.5 | 0 | 0 |
| 28.7 | 0 | 0 |
| 31.1 | 0 | 0 |
| 33.8 | 0 | 0 |
| 36.6 | 92 | 28 |
| 39.7 | 100 | 59 |
| 43.1 | 87 | 85 |
| 46.7 | 36 | 96 |
| 50.6 | 12 | 100 |
| 54.9 | 0 | 100 |
| 59.5 | 0 | 100 |
| 64.6 | 0 | 100 |
| 70.0 | 0 | 100 |
| 75.9 | 0 | 100 |
| 82.3 | 0 | 100 |
| 89.3 | 0 | 100 |
| 96.8 | 0 | 100 |
| 105.0 | 0 | 100 |
| 113.8 | 0 | 100 |
| 123.4 | 0 | 100 |
| 133.8 | 0 | 100 |
| 145.1 | 0 | 100 |
| 157.4 | 0 | 100 |
| 170.6 | 0 | 100 |
| 185.0 | 0 | 100 |
| 200.6 | 0 | 100 |
| 217.6 | 0 | 100 |
| 235.9 | 0 | 100 |
| 255.8 | 0 | 100 |
| 277.4 | 0 | 100 |
| 300.8 | 0 | 100 |
| 326.2 | 0 | 100 |
| 353.7 | 0 | 100 |

Example 6: Particle Size Analysis of Formulation in Example 2

Figure 4:
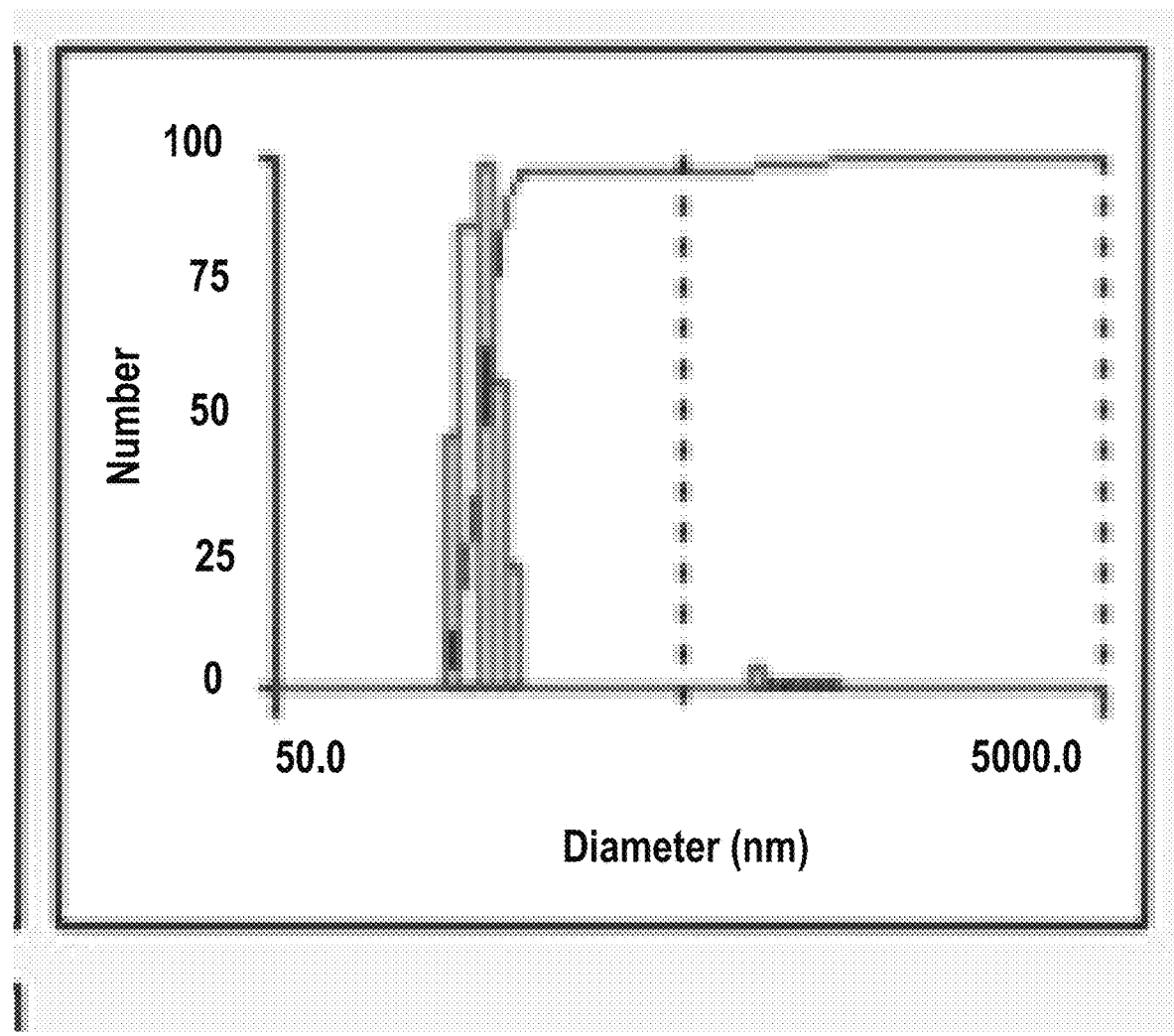
FIG. 4 illustrates a graph quantifying the mean diameter of the particles formulated with Example 2.
Figure 5:
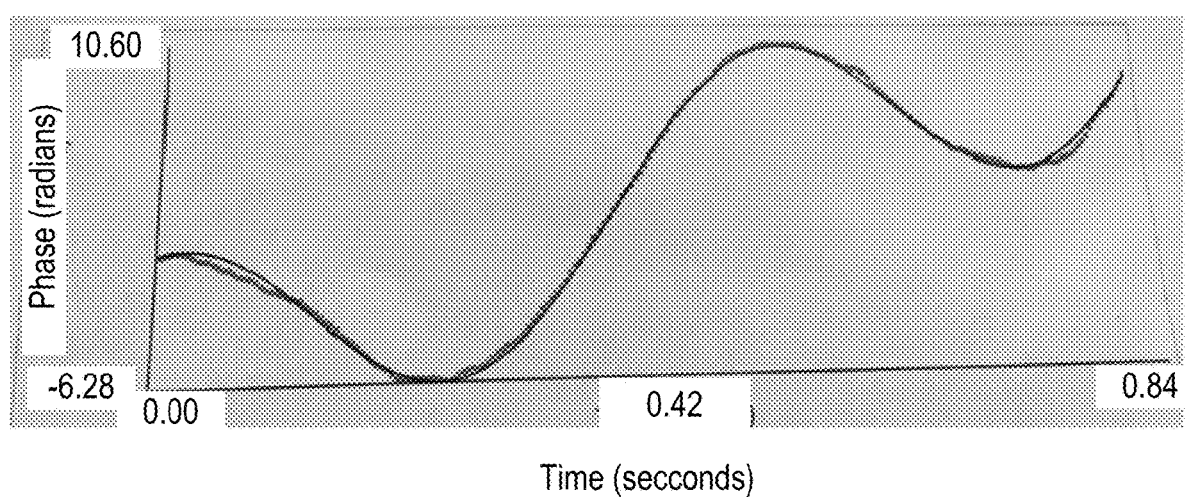
FIG. 5 illustrates a graph quantifying the zeta potential of the particles formulated with Example 2.

The liposomal statin particles including 6.5 wt. % simvastatin and 3.75 wt. % cholesterol of example 2 were found to exhibit a mean diameter (largest linear dimensions) of around 167 nm with a relative variation of 0.206. Data from the testing is provided in Table 2, below, and illustrated in FIG. 4. The zeta-potential was determined to be around −41 mV and is graphed in FIG. 5.

TABLE 2

| Particle size measurements | | |
|---|---|---|
| d (nm) | G (d) | C (d) |
| 105.8 | 0 | 0 |
| 115.0 | 0 | 0 |
| 125.0 | 0 | 0 |
| 136.0 | 48 | 15 |
| 147.8 | 87 | 42 |
| 160.7 | 100 | 74 |
| 174.8 | 57 | 92 |
| 190.0 | 22 | 99 |
| 206.6 | 0 | 99 |
| 224.7 | 0 | 99 |
| 244.3 | 0 | 99 |
| 265.6 | 0 | 99 |
| 288.8 | 0 | 99 |
| 314.1 | 0 | 99 |
| 341.5 | 0 | 99 |
| 371.3 | 0 | 99 |
| 403.7 | 0 | 99 |
| 439.0 | 0 | 99 |
| 477.3 | 0 | 99 |
| 519.0 | 0 | 99 |
| 564.4 | 0 | 99 |
| 613.6 | 0 | 99 |
| 667.2 | 0 | 99 |
| 725.5 | 3 | 100 |
| 788.9 | 0 | 100 |
| 857.7 | 0 | 100 |
| 932.7 | 0 | 100 |
| 1014.1 | 0 | 100 |
| 1102.7 | 0 | 100 |
| 1199.0 | 0 | 100 |
| 1303.7 | 0 | 100 |
| 1417.5 | 0 | 100 |
| 1541.3 | 0 | 100 |

Example 7: Rabbit Ear Hypertrophic Scar Model

Ten New Zealand White rabbits were used in the study, including 3 rabbits for 7.5 wt. % simvastatin with 2.5 wt. % cholesterol in Transcutol/Capmul MCM EP/silicone gel (Kelo-cote®), 4 rabbits for 6.5 wt. % simvastatin with 3.75 wt. % cholesterol in liposome described in Example 2, and 3 rabbits for 6.5 wt. % pravastatin with 2 wt. % cholesterol in liposome described in Example 1. Full-thickness dermal punches were made on the ventral surface of the ear down to but not including the cartilage. The three reagent formulations were applied topically onto wounds at post-operative day (POD) 14 to 25. Samples were harvested after animal euthanasia at POD 28. A 4-µm cross section was stained with hematoxylin & eosin (H&E) and examined under light microscopy. The scar elevation index (SEI) was calculated to quantify the extent of hypertrophic scarring.

Testing Results

In general, it was found that topical treatment with 6.5 wt. % simvastatin with 3.75 wt. % cholesterol in liposome significantly reduced scarring (6.5% simvastatin 1.51±0.07 vs vehicle 1.74±0.10, n=24, p=0.004). Topical treatment with 6.5 wt. % pravastatin with 2 wt. % cholesterol in liposome also significantly reduced scarring (6.5% pravastatin 1.41±0.08 vs vehicle 1.72±0.16, n=16, p=0.02).

Liposomal Statins Reduce the Relative Color/Shade of the Scar Tissue.

Figure 6A:
FIG. 6a provides a photograph of a subject rabbit ear treated with the vehicle.
Figure 6B:
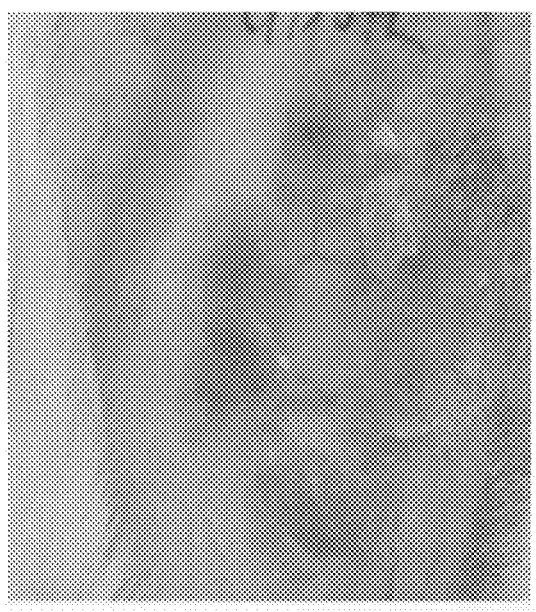
FIG. 6b provides a photograph of a subject rabbit ear treated with the liposomal simvastatin.

As shown in FIGS. 6a and 6b, the simvastatin liposome treated scar tissue has reduced relative color/shade, compared to the control. FIGS. 6a through 6b are photographs of subject ears providing a comparison of relative color/shade of scar tissue of liposomal simvastatin vs. liposomal control which was made from the same lipids shown in Example 1 but contained no drug. Treatment was shown to reduce the color/shade of scar tissue relative to the normal skin.

Figure 7A:
FIG. 7a provides a photograph of a subject rabbit ear treated with the vehicle.
Figure 7B:
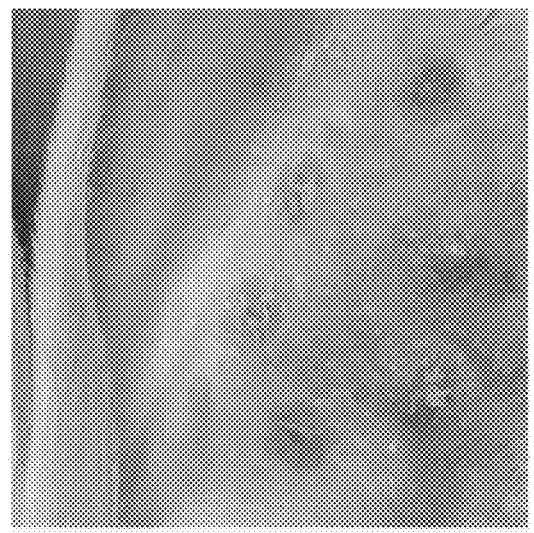
FIG. 7b provides a photograph of a subject rabbit ear treated with the liposomal pravastatin.

Similarly, as shown in FIGS. 7a and 7b, the pravastatin liposome treated scar tissue has reduced relative color/shade, compared to the control. FIGS. 7a through 7b are photographs of subject ears providing a comparison of relative color/shade of scar tissue of liposomal pravastatin vs. liposomal control (no drug). Treatment was shown to reduce the color/shade of scar tissue relative to the normal skin.

Figure 8A:
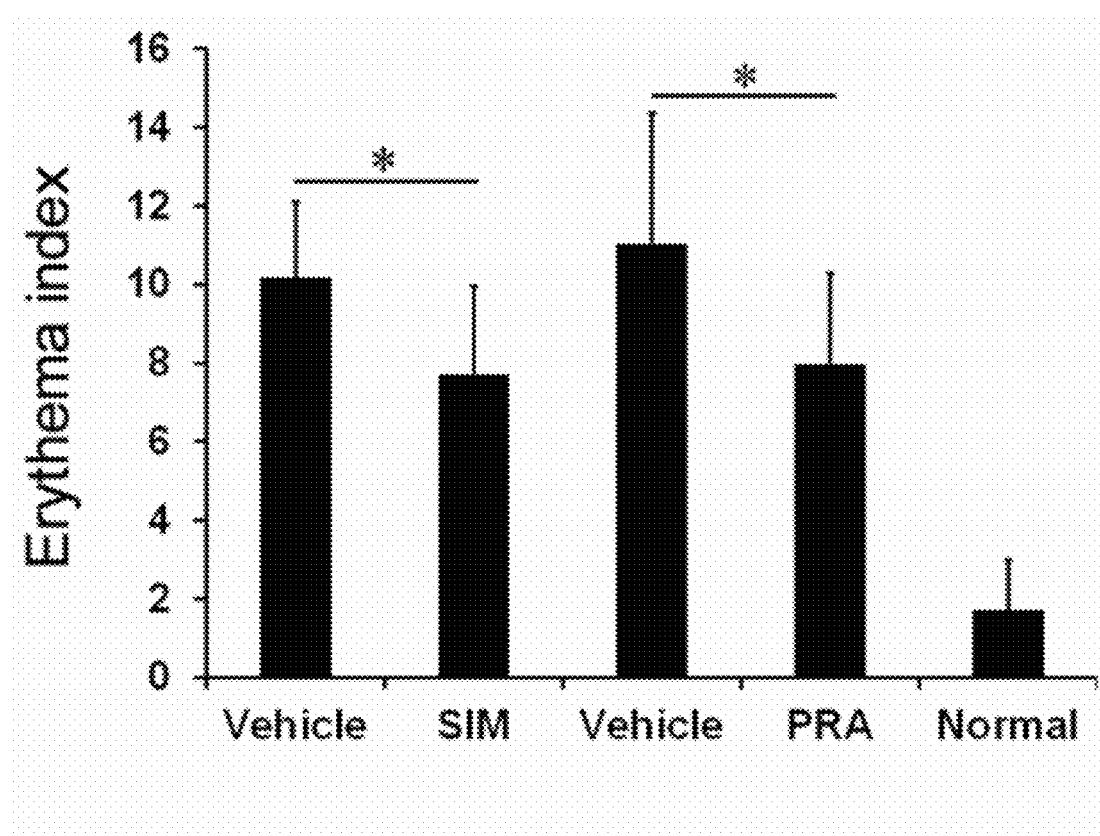
FIG. 8a provides a graph of the relative erythema color/shade index of the ear punches after treatment with the vehicle vs. the liposomal simvastatin.
Figure 8B:
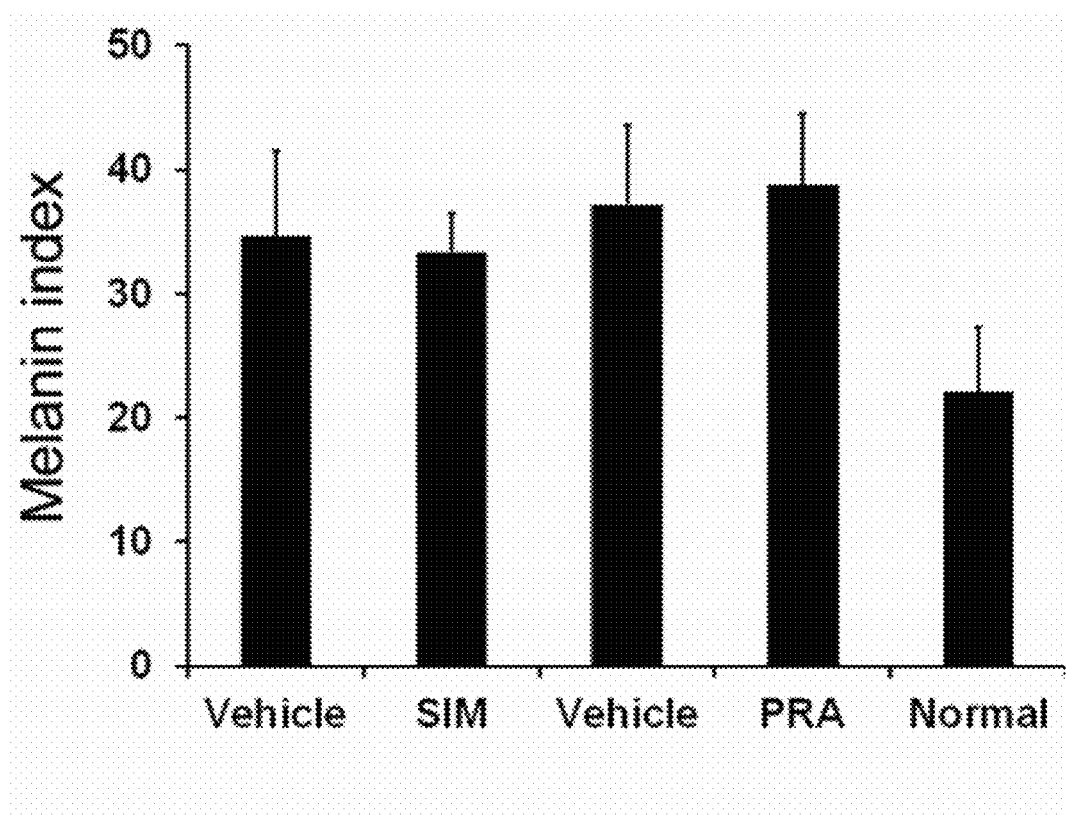
FIG. 8b provides a graph of the relative melanin color/shade of the ear punches after treatment with the vehicle vs. the liposomal pravastatin.

FIG. 8a graphically quantifies the erythema index (redness) color/shade of the ear punches after treatment with the vehicle, liposomal simvastatin, and liposomal pravastatin. As can be seen, erythema (redness) is reduced in the statin treated punches are compared to the vehicle. FIG. 8b graphically quantifies the melanin color/shade of the ear punches after treatment with the vehicle, liposomal simvastatin, and liposomal pravastatin.

Liposomal Statins Reduce the Scar Elevation Index (SEI).

Figure 9A:
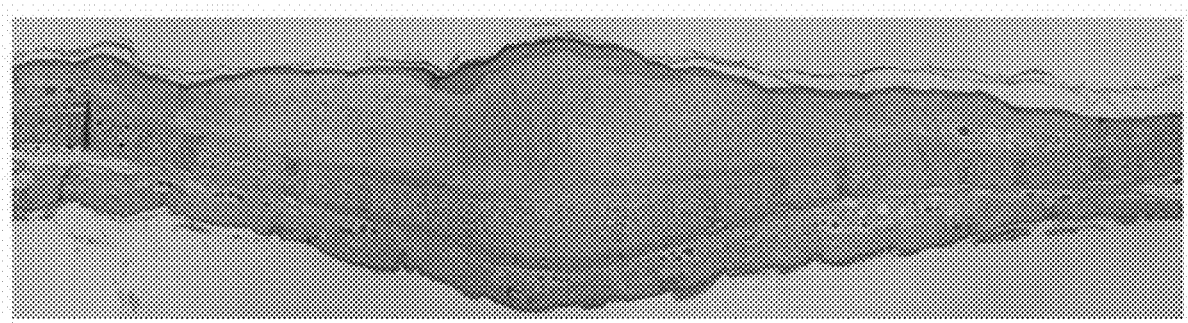
FIG. 9a is a photograph of a cross-section of wounded rabbit skin treated with the vehicle taken under a microscope.
Figure 9B:
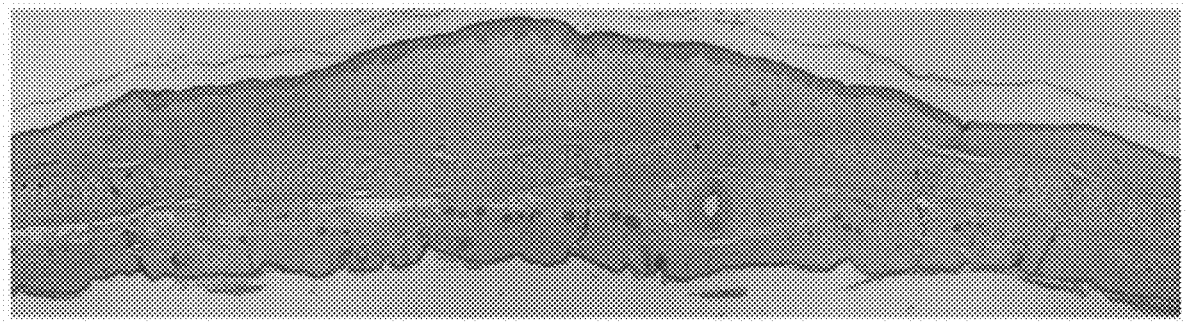
FIG. 9b is a photograph of a cross-section of wounded rabbit skin treated with the 6.5 wt % of pravastatin taken under a microscope.
Figure 9C:
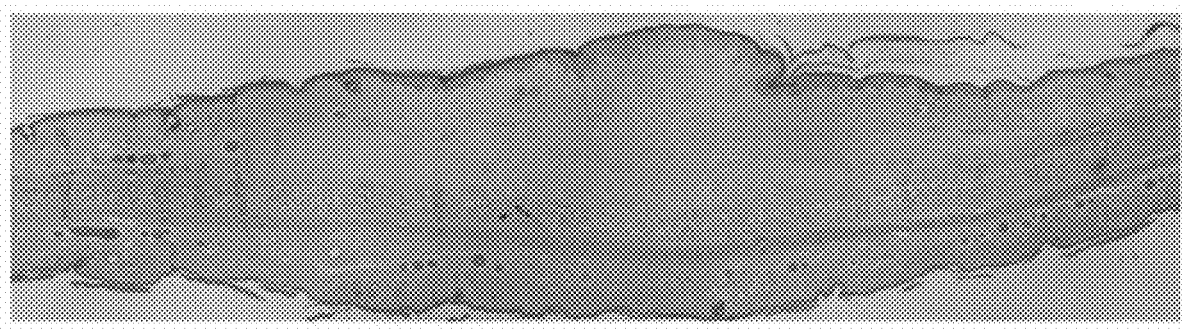
FIG. 9c is a photograph of a cross-section of wounded rabbit skin treated with the vehicle take taken under a microscope.
Figure 9D:
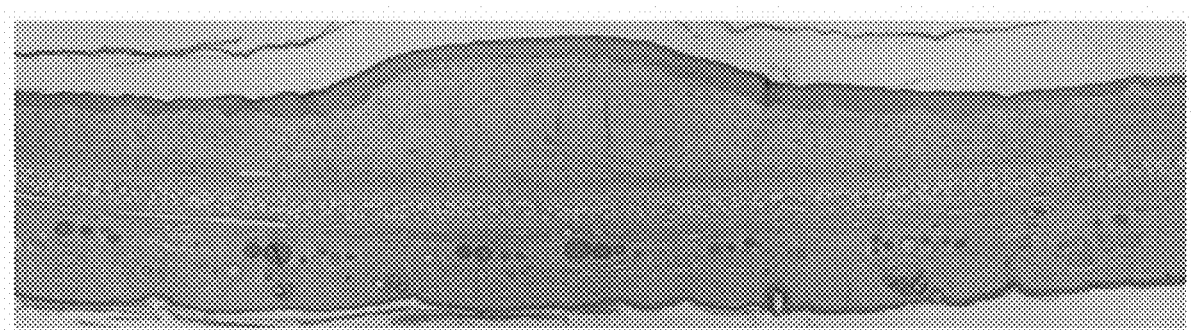
FIG. 9d is a photograph of a cross-section of wounded rabbit skin treated with the 6.5 wt % of simvastatin taken under a microscope.
Figure 9E:
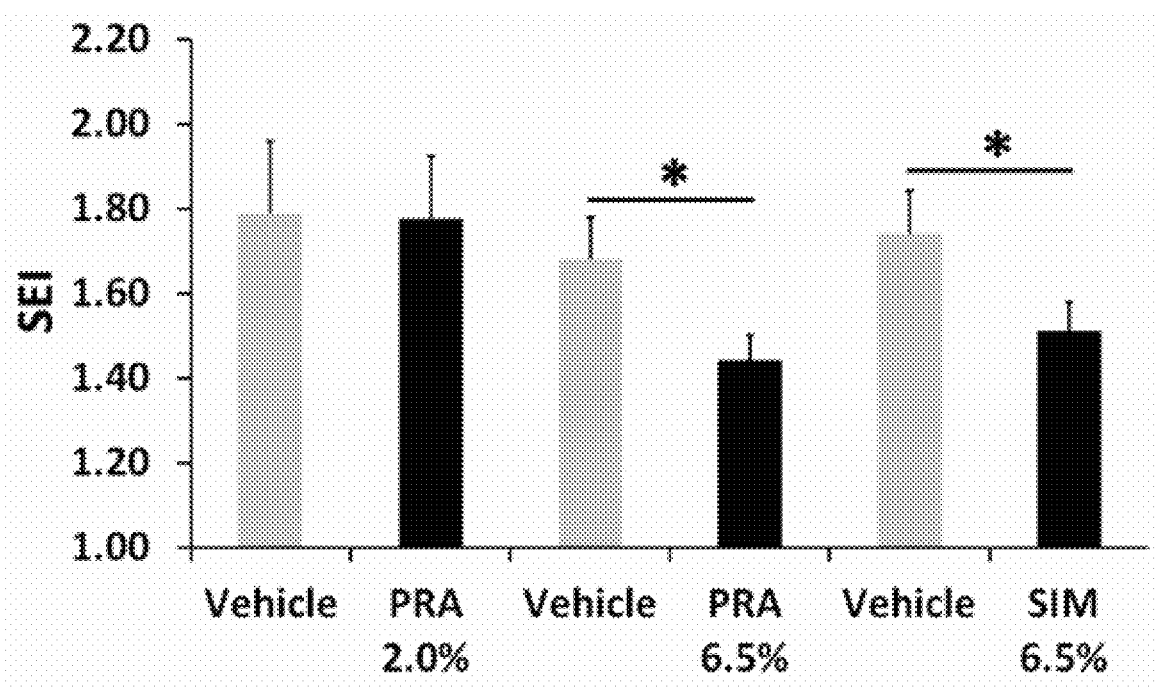
FIG. 9e provides a graph illustrating the reduction of the SEI using the liposomal statin treatments (either pravastatin or simvastatin) compared to control (*indicates significant difference, P<0.05)
Figure 9F:
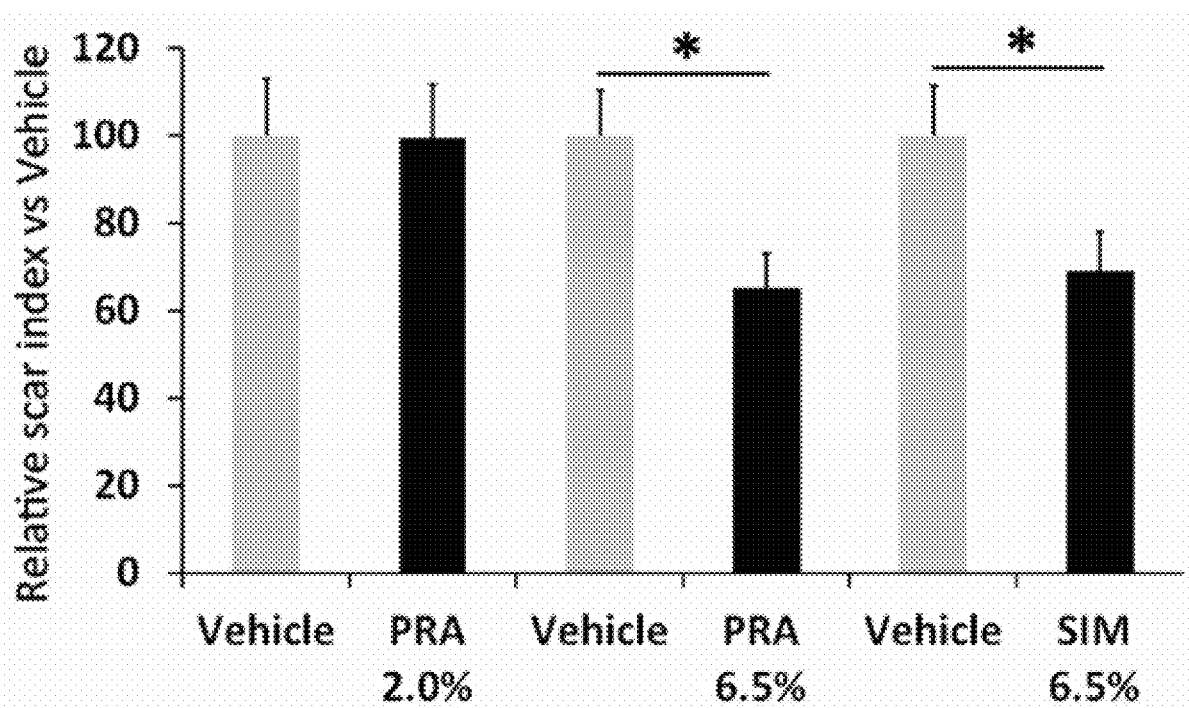
FIG. 9f provides a graph illustrating the relative scar index using the liposomal statin treatments (either pravastatin or simvastatin) compared to control (*indicates significant difference, P<0.05)
Figure 10A:
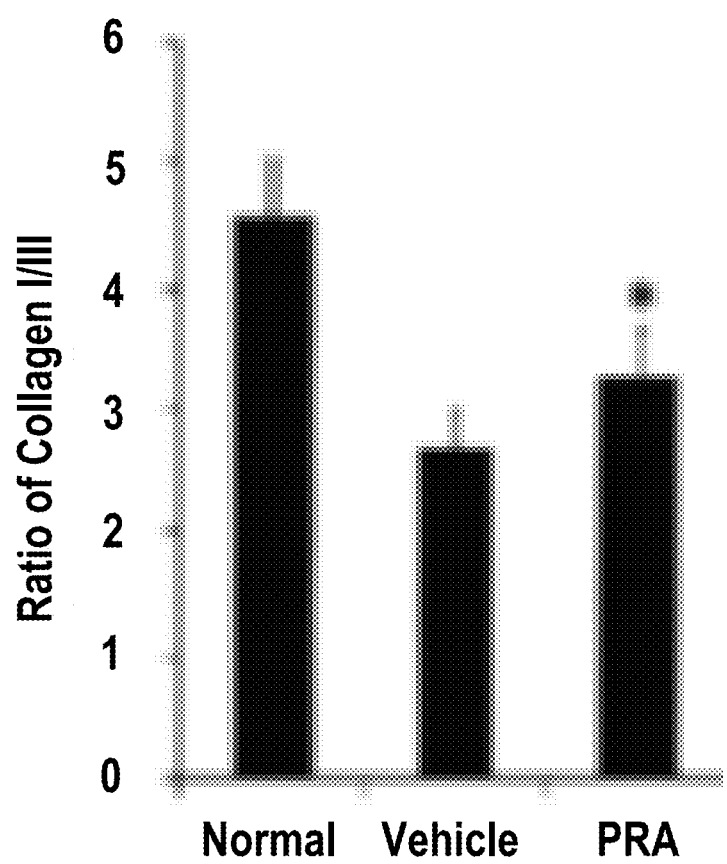
FIG. 10a is a graph of the relative ratios of Collagen I/III between the vehicle and treated samples.
Figure 10D:
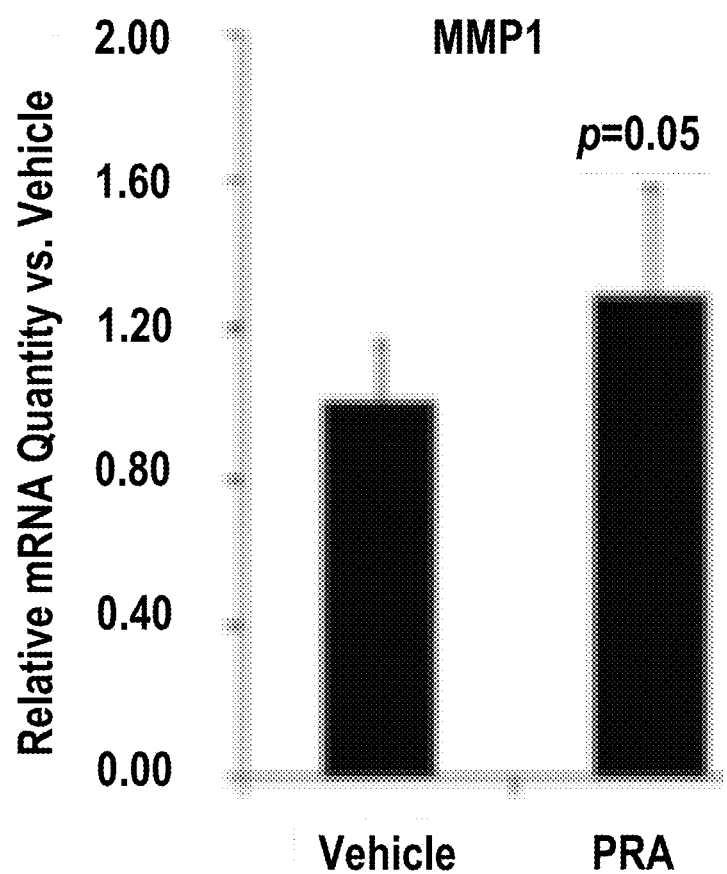
FIG. 10d is a graph of the relative mRNA quantity of MMP1.
Figure 10E:
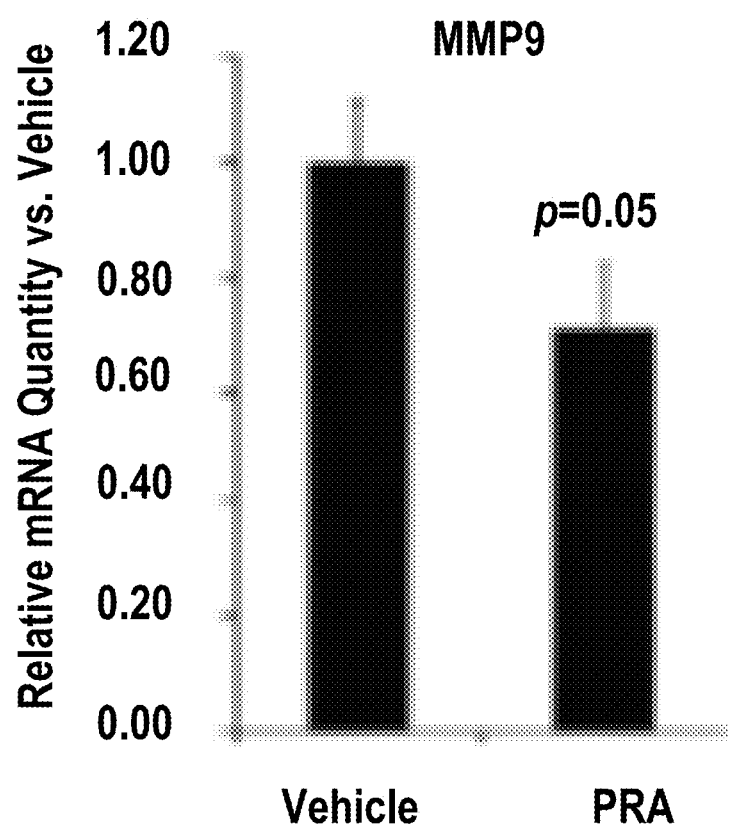
FIG. 10e is a graph of the relative mRNA quantity of MMP9.
Figure 10F:
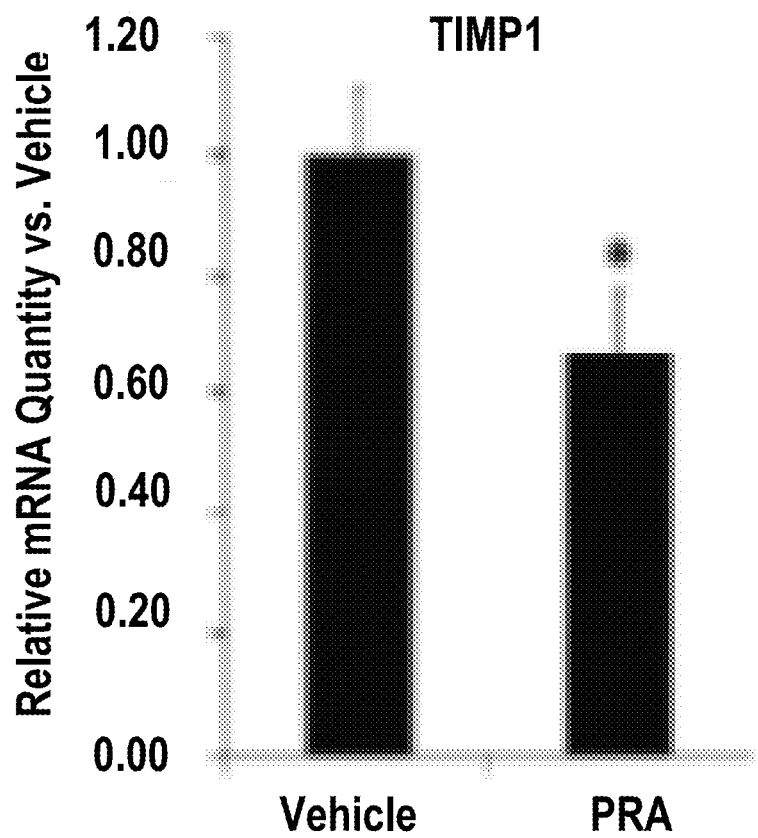
FIG. 10f is a graph of the relative mRNA quantity of TIMP1.
Figures 10G, 10H:
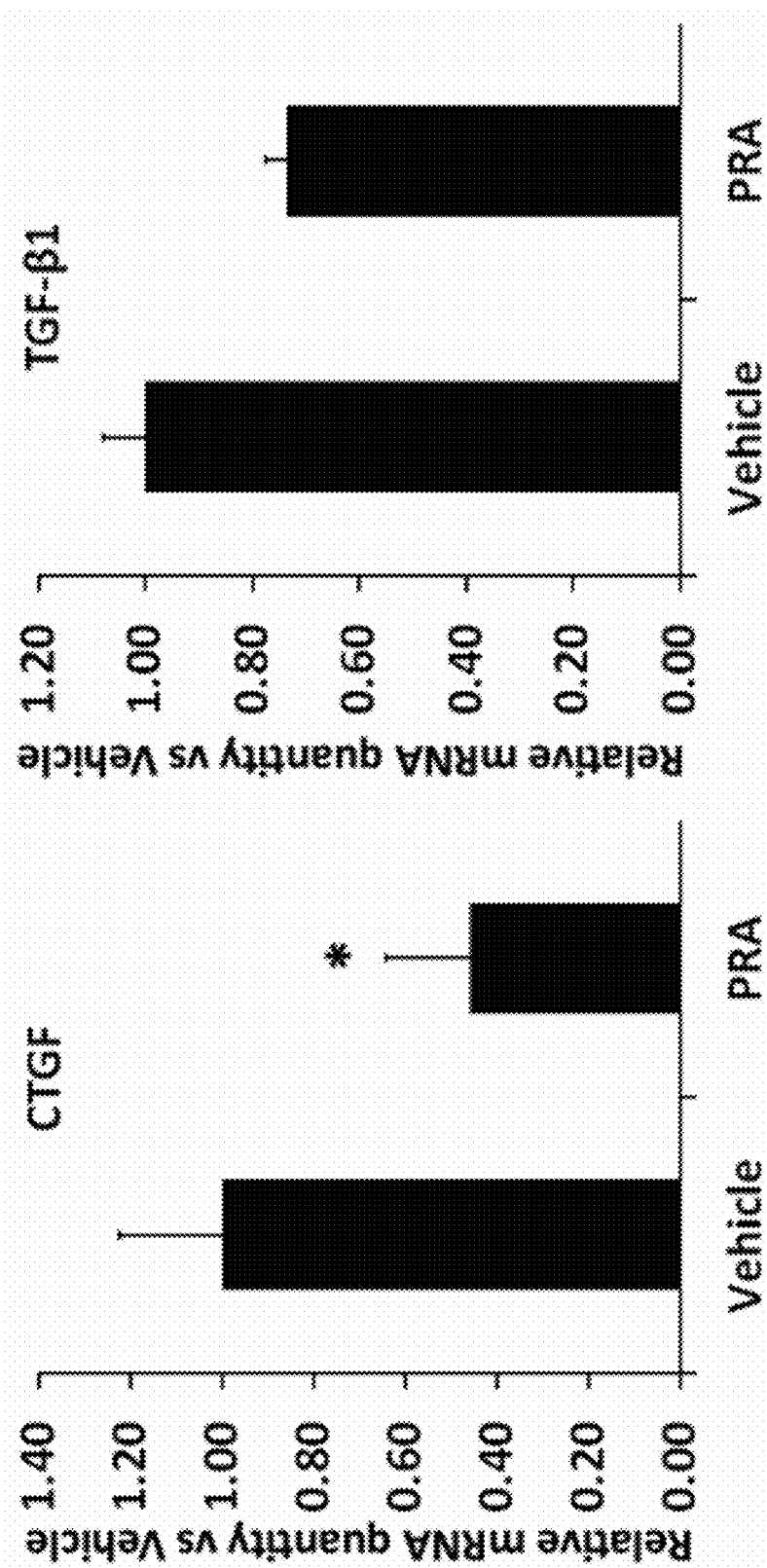
FIG. 10g is a graph of the relative ratio of CTGF expression.
FIG. 10h is a graph of the relative ratio of TGFβ1 expression.

FIGS. 9a and 9b are photographic images of a cross-section of rabbit skin, wherein FIG. 9a depicts skin treated with the vehicle and FIG. 9b depicts skin treated with 6.5 wt. % of pravastatin. FIGS. 9c and 9d are images of a cross-section of rabbit skin, wherein FIG. 9c depicts skin treated with the vehicle (empty liposomes) and FIG. 9d depicts skin treated with 6.5 wt. % simvastatin. FIG. 9e provides a graph illustrating the reduction of the SEI using the liposomal statin treatments (either pravastatin or simvastatin) compared to control (*indicates significant difference, P<0.05). FIG. 9f provides a graph illustrating the relative scar index using the liposomal statin treatments (either pravastatin or simvastatin) compared to control (*indicates significant difference, P<0.05). The data suggests the dosage may relatively important as it was found that liposomal pravastatin at (2 wt. %) did not reduce SEI.

Liposomal Statins Reduced the mRNA Level of Genes Contributing to Scar Tissue Formation.

Pravastatin liposomal statin treated scar tissue, using the formulation of example 1, resulted in collagen I/collagen III ratios closer to normal skin tissue compared to vehicle treated scar tissue. FIGS. 10a through 10h illustrate relative ratios of collagen I/III, Col1A1, Col3A1, MMP9 (inflammatory marker), TIMP1, TGF-β1, and connective tissue growth factor (CTGF), which contribute to the scar formation, with the liposomal formulation vs. the vehicle control. Liposomal statin was also found to increase the MMP1 (collagenase).

Liposomal Statins Reduced the CD31-Expressing Micro-Vessels.

Figure 11A:
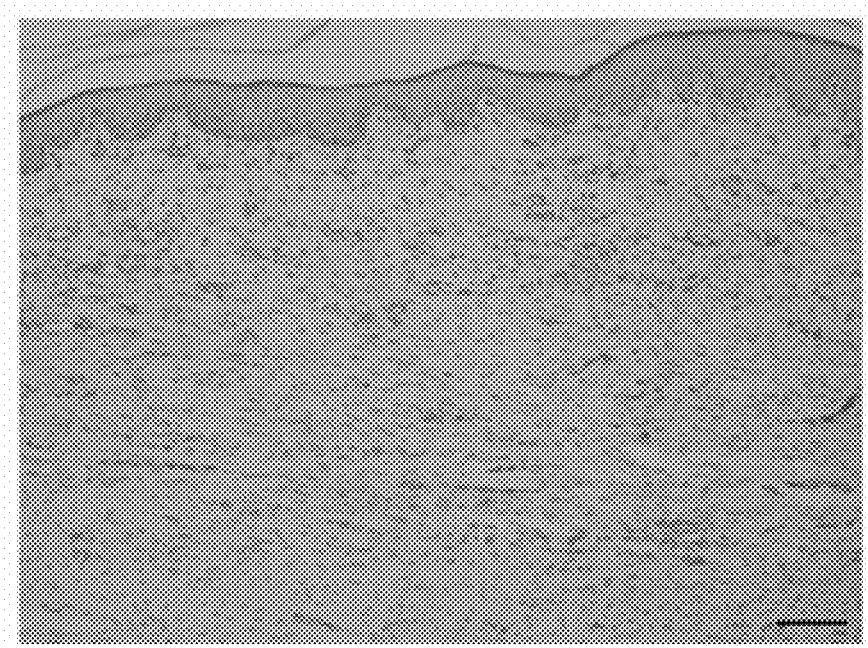
FIG. 11a is a photograph of CD31 immunohistology of scar tissue of treated with vehicle.
Figure 11B:
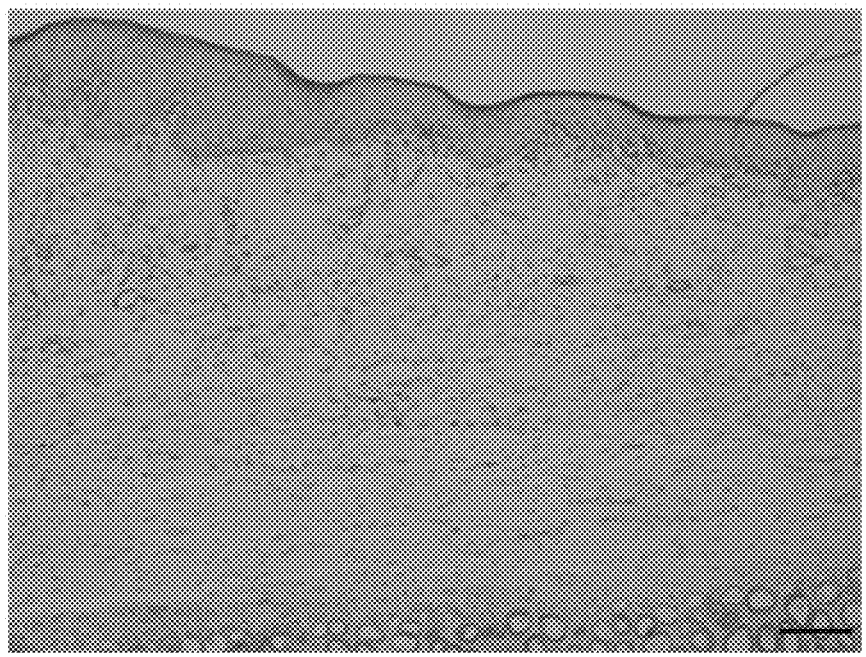
FIG. 11b is a photograph of CD31 immunohistology of scar tissue of treated with vehicle.
Figure 11C:
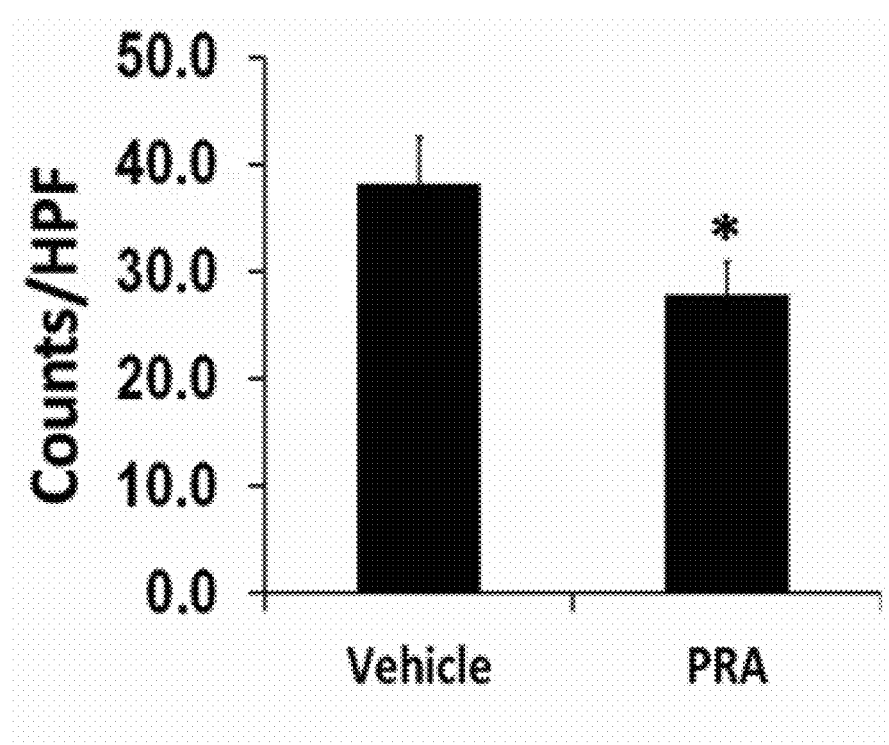
FIG. 11c is graph of the count of CD31 expressed microvessels.

Immunostaining using CD31-antibody of scar tissue indicated that liposomal statin treatment resulted in relatively lower amounts of CD31-expressing microvessels, a further indication of regressive scarring due to treatment. CD31 expressing microvessels were counted separately in high-power fields (HPFs). FIGS. 11a and 11b are images of immunostained scar tissue of vehicle only and the pravastatin liposomal formulation of Example 1. FIG. 11c is a graph of the CD31 expressing microvessels counted separately in high power fields for the vehicle only and pravastatin.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:
1. A method of preparing liposomal statins comprising:
  (a) preparing a lipid solution including phosphatidylcholine, cholesterol, a skin penetrating surfactant, an organic solvent, and optionally vitamin E;
  (b) removing said solvent from said lipid solution and forming a lipid cake;
  (c) hydrating said lipid cake with a first aqueous media;
  (d) mixing said lipid cake in a mixer and subjecting said lipid cake to one or more freeze/thaw cycles;
  (e) extruding said lipid cake;
  (f) optionally adding a cryo-protective agent;
  (g) lyophilizing to provide a powder liposomal statin; and
  (h) reconstituting the powder liposomal statin with a second aqueous media to provide a liposomal statin formulation;
wherein:
  a statin is added to said lipid solution in step (a) or to said first aqueous media used in step (c), said statin comprising simvastatin, lovastatin or pravastatin; and
  said liposomal statin formulation comprises:
    said phosphatidylcholine in an amount ranging from 15 wt. % to 40 wt. %;
    said cholesterol in an amount ranging from 1 wt. % to 5 wt. %;
    said skin penetrating surfactant in an amount ranging from 2 wt. % to 15 wt. %;
    said Vitamin E in an amount ranging from 0 to 5 wt. %;
    said cryo-protective agent in an amount ranging from 0 wt. % to 15 wt. %; and
    the balance said second aqueous media;
    wherein the total amount of said phosphatidylcholine, cholesterol, skin penetrating surfactant, Vitamin E, cryo-protective agent, statin, and second aqueous media equal 100% of said liposomal statin formulation.

2. The method of claim 1, wherein said Vitamin E is present in said lipid solution, and said liposomal statin formulation comprises said Vitamin E in an amount ranging from 1 wt. % to 5 wt. %.

3. The method of claim 1, further comprising drying said lipid cake prior to hydrating said lipid cake.

4. The method of claim 1, wherein said statin added to said lipid solution in step (a) comprises lovastatin and/or simvastatin and wherein said statin added to said aqueous media in step (c) comprises pravastatin.

5. The method of claim 1, wherein said liposomal stain formulation comprises said cryo-protective agent in an amount ranging from 5 wt. % to 15 wt. %.

6. The method of claim 1, wherein said phosphatidylcholine is sourced from soy or egg yolk.

7. The method of claim 1, wherein said first aqueous media comprises water or a phosphate buffered saline.

8. The method of claim 1, wherein said cake is extruded through a membrane having a pore size in the range of 0.1 μm to 0.2 μm.

9. The method of claim 1, wherein said lipid cake is extruded through at least two membranes.

10. A method of applying a liposomal statin formulation, comprising:
providing a topical formulation of liposomal statins comprising phosphatidylcholine present in the range of 15 wt. % to 40 wt. %, cholesterol present in the range of 1 wt. % to 5 wt. %, vitamin-E present in the range of 0 wt. % to 5 wt. %, a skin penetrating surfactant present in the range of 2 wt. % to 15 wt. %, a cryo-protector present in the range of 0 wt. % to 15 wt. %, a statin comprising simvastatin, lovastatin or pravastatin present in the range of 0.1 wt. % to 10 wt. %, and the balance aqueous media, wherein the total amount of said phosphatidylcholine, cholesterol, skin penetrating surfactant, Vitamin E, cryo-protector, statin, and second aqueous media equal 100% of said liposomal statin formulation; and
applying said formulation onto a subject to a wound and reducing hypertropic scarring.

11. The method of claim 10, wherein said Vitamin E is present in said formulation in an amount ranging from 1 wt. % to 5 wt. %.

12. The method of claim 10, wherein said cryo-protector is present in said formulation in an amount ranging from 5 wt. % to 15 wt. %.

13. A formulation of liposomal statins comprising:
phosphatidylcholine present in the range of 15 wt. % to 40 wt. %;
cholesterol present in the range of 1 wt. % to 5 wt. %;
vitamin-E present in the range of 0 wt. % to 5 wt. %;
a skin penetrating surfactant present in the range of 2 wt. % to 15 wt. %;
a cryo-protector present in the range of 0 wt. % to 15 wt. %;
a statin comprising simvastatin, lovastatin or pravastatin present in the range of 0.1 wt. % to 10 wt. %; and
the balance aqueous media, wherein the total amount of said phosphatidylcholine, cholesterol, skin penetrating surfactant, Vitamin E, cryo-protector, statin, and second aqueous media equal 100% of said liposomal statin formulation.

14. The formulation of claim 13 wherein said skin penetrating surfactant comprises sorbitan laurate.

15. The formulation of claim 13 wherein said skin penetrating surfactant comprises sorbitan stearate.

16. The formulation of claim 13 wherein said skin penetrating surfactant comprises sodium cholate.

17. The formulation of claim 13, wherein said Vitamin E is present in said formulation in an amount ranging from 1 wt. % to 5 wt. %.

18. The formulation of claim 13, wherein said cryo-protector is present in said formulation in an amount ranging from 5 wt. % to 15 wt. %.

* * * * *